United States Patent [19]

Monthony et al.

[11] Patent Number: 4,749,655
[45] Date of Patent: Jun. 7, 1988

[54] SPECIMEN COLLECTION PACKAGE

[75] Inventors: James F. Monthony, Timonium; Virginia M. Corasaniti, Baltimore; C. Michael Gosnell, Fallston, all of Md.

[73] Assignee: Becton Dickinson and Company, Franklin Lakes, N.J.

[21] Appl. No.: 56,081

[22] Filed: Jun. 1, 1987

[51] Int. Cl.$^4$ ............................................. C12M 1/30
[52] U.S. Cl. .................................. 435/295; 435/292; 604/1
[58] Field of Search .................. 128/759, 749; 604/1; 435/287, 292, 295, 296, 299, 300

[56] References Cited

U.S. PATENT DOCUMENTS

| | | | |
|---|---|---|---|
| 3,450,129 | 6/1969 | Avery | 128/2 |
| 4,014,748 | 3/1977 | Spinner et al. | 435/295 |
| 4,175,008 | 11/1979 | White | 435/295 |
| 4,223,093 | 9/1980 | Newman et al. | 435/295 |
| 4,311,792 | 1/1982 | Avery | 435/30 |
| 4,353,868 | 10/1982 | Joslin et al. | 435/295 |
| 4,604,360 | 8/1986 | Hounsell | 435/295 |

OTHER PUBLICATIONS

Stuart, R. D. et al. "The Problem of Transport of Specimens for Culture of Gonococci", Canadian J. of Pub. Health, 1954, 45 pp. 78-83.
Amies, C. P. et al. "A Modified Formula for the Preparation of Stuart's Transport Medium", Canadian J. of Pub. Health, 1967, 58 pp. 296-300.
Ellner, P. D. et al. "Survival of Bacteria on Swabs." J. Bacteriology, Feb. 1966, vol. 91, No. 2, pp. 905-906.
Barry, A. L. et al. "Efficiency of a Transport Medium for the Recovery of Aerobic and Anaerobic Bacteria from Application Swabs", Applied Microbiology, Jul. 1972, vol. 24, pp. 31-33.
Ross et al. "Swabs and Swab-transport Media Kits in the Isolation of Upper Respiratory Bacteria", J. Clin. Pathol, 1982, vol. 35, pp. 223-227.

Primary Examiner—James C. Yeung
Assistant Examiner—Noah Kamen
Attorney, Agent, or Firm—James R. McBride

[57] ABSTRACT

A self-contained specimen collecting and transporting unit is provided which has all of the advantages of the known specimen collecting and transporting units and which is characterized by the ability to preserve microorganisms during the transporting thereof in the transporting unit. The improved specimen collecting and transporting unit has a pledget composed of carbon fiber. The use of a carbon fiber pledget has been found to have a synergistic effect in preserving the viability of microorganisms which are obtained by use of the swab of the specimen collecting and transporting unit.

5 Claims, 1 Drawing Sheet

SPECIMEN COLLECTION PACKAGE

BACKGROUND OF THE INVENTION

The present invention relates generally to swabs used by physicians for collecting a specimen from a patient and for keeping any microorganisms contained in the specimen alive for a period of time after it has been collected. Such swabs customarily include an absorbent swabbing tip carried on the end of an elongated stem. The specimen is collected by holding the stem and by swabbing a particular area of the patient's body with the absorbent.

More particularly, specimen collecting swabs are usually packaged with a transport container having its own supply of culture-sustaining media. After the specimen has been collected, the swab is placed into the container with the swabbing tip in contact with the media so as to keep any microorganisms contained in the specimen alive until the transport container can be moved to a laboratory for testing. The container serves to protect the specimen from contamination with environmental microorganisms. It is also necessary to provide the components of the container in a sterile form.

PRIOR ART

Numerous specimen transporting packages are known. One commercially successful specimen collecting and transporting package is disclosed in U.S. Pat. No. 3,450,129 to Avery. The transporting unit includes a flexible outer tube within which is contained a frangible ampoule having a liquid culture-sustaining media sealed therein. After the specimen has been collected by the swab, the swab is placed in the tube and the tube is squeezed to break the ampoule and release the liquid. The liquid moistens an absorbent plug, usually referred to as a pledget, which is disposed within the tube in engagement with the tip of the swab so as to keep the tip moist and to restrain the media until the specimen in the package can be transported and tested. A cap is placed over the tube to keep the inside of the tube protected from contamination during transport.

Another culture and transporting unit is described in U.S. Pat. No. 4,311,792 to Avery. This patent provides a swab on a flexible elongated stem and is provided with means whereby the length of the elongated stem can be adjusted to provide a flexible stem for insertion into suitable cavities of the body.

U.S. Pat. No. 4,175,008 to White, describes a culture specimen collection and transport package wherein a deformable piston is disposed within a tube containing a culture-sustaining medium. At the time of use, the swab is used to displace the piston downwardly within the tube so as to force the culture-sustaining media past the piston into engagement with the swab. A pledget may be disposed between the swab and the piston for the same purpose as described hereinabove in connection with the Avery U.S. Pat. No. 3,450,129.

A problem which has confronted the use of specimen collection and transporting units utilizing a swab for specimen collection is maintaining the viability of any microorganisms which are collected by the swab. In spite of the utilization of a high level of skill and care in collecting the specimen so as to prevent contamination of the specimen, viability of the microorganisms is not assured by the use of the prior art devices heretofore described. Accordingly, there is a need to improve the viability of microorganisms obtained by specimen collection and transporting devices so as to assure that any microorganisms contained in the specimen remain viable through the entire specimen collection, transportation, storage and subsequent identification phases of developing the specimen.

SUMMARY OF THE INVENTION

Generally, in accordance with the invention a new and improved self-contained specimen collecting and transporting unit is provided which has all of the advantages of the known specimen collecting and transporting units and which is characterized by the ability to preserve microorganisms during the transporting thereof in the transporting unit. The improved specimen collecting and transporting unit has a pledget composed of carbon fiber. The use of a carbon fiber pledget has been found to have a synergistic effect in preserving the viability of microorganims which are obtained by use of the swab of the specimen collecting and transporting unit.

BRIEF DESCRITION OF THE DRAWINGS

DETAILED DESCRIPTION OF THE PREFERRED EMBODIMENT

Figures 1, 2:
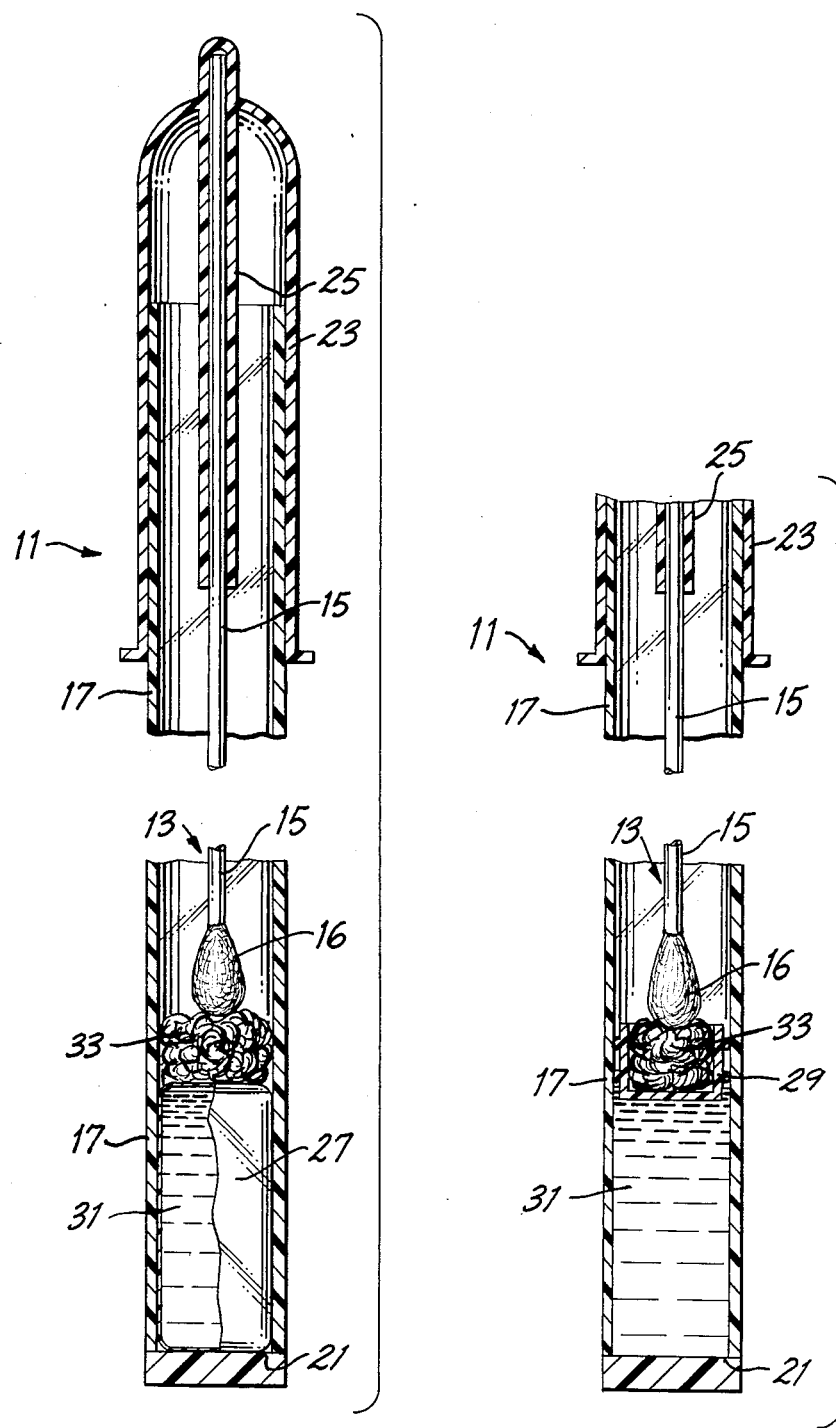
FIG. 1 is a cross-sectional view of an ampoule type specimen collection and transporting unit of the known type.
FIG. 2 is a cross-sectional view of a specimen collection and transporting unit which utilizes a piston to restrain a culture-sustaining media.

As shown in the drawings, in which like reference characters represent like elements, there is shown in FIG. 1 the component parts of a specimen collection and transporting unit 11 whose components are used in collecting a bacterial specimen from a patient's body and for maintaining the microorganisms present in the specimen in a live condition until such time as the specimen can be transported to a laboratory and tested. The transporting unit comprises a swab 13 which includes a stem 15 and a swabbing tip 16. A tube 17 is provided for holding the swab both before and after the bacterial specimen is collected.

The elongated stem 15 carries an absorbent swabbing material 16 on its inner end upon which the bacterial specimen is collected. The swabbing material may be made from cellulose, alginates polyesters, or other soft and absorbent materials which are suitable for the collection of clinical specimens. Such absorbent swabbing materials are well known in the art of collecting bacterial specimens.

The tube 17 is preferably made of a flexible plastic material. One end of the tube 17 is closed off by a heat seal 21 while the other end of the tube is open. A tubular plastic cap 23 is adapted to fit closely but to slide freely over the outer end portion of the tube to close the tube both before and after the swab 13 is used. At its outer end, the plastic cap is formed with a reduced diameter tubular neck 25 which is adapted to receive the outer end portion of the stem 15. The stem 15 may fit into the tubular neck 25 in a manner to provide a snug but slidable fit. In some instances, the cap is used as a handle for the swab when the culture is taken.

As shown in FIG. 1, disposed within the inner end portion of the tube 17 and located adjacent the heat seal 21 is a sealed ampoule 27 of a frangible material. The ampoule is filled with a liquid culture-sustaining transport media. As shown in FIG. 2, a piston 29 is provided to restrain a liquid culture-sustaining media 31. A piston type specimen collection and transporting unit is described in U.S. Pat. No. 4,223,093 to Newman et al.

In FIG. 1, the ampoule 27 is located in the lower end portion of the tube 17 below a pledget 33. In FIG. 2, the pledget 33 is disposed within a recess in the piston 29.

The assembled specimen transporting unit, as shown in FIGS. 1 and 2, is packaged within a substantially flat envelope (not shown) made of a suitable material which enables the specimen transporting unit to be sterilized by autoclaving, irradiation or the like after the unit has been sealed in the envelope. The entire transporting unit is maintained in a sterile condition until such time as the envelope is opened.

In the process of collecting a specimen, the cap 23 is removed from the tube 17 and the swab 13 is pulled out of the tube. A suitable area of the patient is swabbed with the tip to obtain a bacterial specimen. Thereafter, the swab and the cap are returned to the tube with the tip of the swab being positioned in contact with the pledget 33. In the case of the transporting unit of FIG. 1, the tube is squeezed or pinched adjacent to the ampoule 27 to break the ampoule and release the liquid therein. In the case of the transporting unit of FIG. 2, the tip of the swab is used to force the piston 29 downwardly in the tube to release the culture-sustaining media into contact with the pledget 33 and the tip of the swab. In both cases the liquid culture-sustaining media moistens the pledget 33 which, in turn, moistens the tip of the swab to keep the culture in a live condition until it reaches a laboratory for testing.

In accordance with the invention, the pledget 33 is made from a carbon fiber, preferably from carbon fiber cloth material. It has unexpectedly been discovered that the use of carbon fiber for the purpose of forming the pledget 33 or the swabbing material 16 results in a synergistic effect in respect to maintaining the viability of a bacterial specimen collected on the swab of the bacterial collection and transporting unit of the invention. As used herein the term "carbon fiber" includes materials commonly referred to as graphite fiber and carbon fiber. Graphite and carbon fiber thread and cloth are well known items of commerce and can be obtained from a variety of manufacturers. Their primary usage is as a strength building component of composite materials (e.q. a replacement for glass cloth in a fiberglass type material). Graphite fibers and carbon fibers can be differentiated chemically and/or physically, but the terms graphite fiber cloth or carbon fiber cloth are often used interchangeably. Both are typically 95% carbon in composition and differ in their molecular organization but not their elemental composition.

Carbon fibers are significantly different from powdered forms of carbon, both in method of manufacture and in physical form. There is no particular criticality for the thread size or weave for the carbon fiber cloth utilized in the invention. It is likely that a plurality of smaller diameter individual fibers in each "thread" of material, such as Thornel TM 300 carbon fiber cloth from Union Carbide (1000 fibers in each thread) does provide a greater surface area and adds to the suitability of cloth woven from such a thread. Large diameter mono-filament cloths would approach solid "plugs" or "sheets" of material in surface area and are less suitable. While not wishing to be bound by any theory, it is believed that the carbon fiber cloth may remove, by absorption, harmful components in the culture sustaining media. This enhances the recovery of viable organisms collected on the swab.

The following examples further illustrate various features of the invention and show the improved nature of the bacterial collection and transporting unit of the invention over those transporting units heretofore used in the prior art.

The invention relates to the use of a novel material for the pledget or swabbing tip of a typical culture transport device. Cloth woven from carbon fibers was cut to a size of about one inch square and used as a replacement for the pledget or swabbing tip supplied with commercial transport devices. The carbon fiber cloth was sterilized before insertion into the device by a suitable technique, such as by the common technique of flame sterilization. The swabbing tip of the device was used to absorb a known quantity of a suspension of a test organism, inserted into the device and the culture sustaining media released to wet the graphite pledget and the swab. For the demonstration of enhanced maintenance of viability of the test organism, the devices were similarly inoculated and utilized with the pledget or swabbing tip materials supplied by the manufacturer. The devices were stored for various periods of time and the recovery of the test organisms was assessed by inoculating an agar containing growth media petri plate and incubating at 37 deg C. The level of growth, if any, was recorded.

Several test organisms were examined. In all instances, the use of the carbon fiber cloth pledget either extended the time period during which the test organism could be recovered or was equal to that obtained with the original pledget. In no instance was the carbon fiber cloth material found to produce an inferior result. As shown in Tables 1, 2, and 3 several of the test organisms could not be recovered from conventional devices at time periods exceeding four hours. Increased levels of recovery were observed utilizing the devices which incorporated the carbon fiber cloth pledget. The beneficial effect of the carbon fiber cloth material was high. The use of the carbon fiber cloth material described herein does not add to the complexity of the manufacturing procedure. No significant residue is carried over to the sample in the final analytical procedures. Any carry over from the pledget is of a fibrous nature and is less objectionable than a granular material such as powdered charcoal.

While the examples deal with the use of graphite fiber woven cloth, the beneficial properties reported herein are not related to the specific form of the carbon fiber member of the transport device. A non-woven fabric or a carbon fiber wool pledget is equally advantageous. Woven fabric which is manufactured from a composite of a carbon fiber and a normal fiber such as cotton, rayon or a polyester is contemplated as a means of providing the beneficial effects of the carbon fiber pledget or swabbing tip at a reduced cost.

EXAMPLE 1

Representative fastidious organisms utilized were *Haemophilus influenzae, Neisseria meningitidis* and *Neisseria gonorrhoeae.* The non-fastidious organism *Streptococcus pyogenes* (group A Strep) was also studied. These organisms are common human pathogens and are typical of the type of organism which may be sampled from a patient utilizing swab type sample devices. After growth in broth culture media, suspensions of the organisms were diluted and their turbidity measured in a spectrophotometer. The technique of quantitative plate counts was utilized to allow construction of a graph relating the optical density to the number of organisms present. Subsequently, the number of organisms in a suspension was estimated by measurement of the optical density of the suspension and reading the concentration from the corresponding graph. Suspensions were produced that contained approximately $5 \times 10^8$ colony forming units (CFU) per milliliter (ml.). A 0.20 ml aliquot of the standard suspension of organisms was inoculated by placement in a sterile test tube and allowing the aliquot to be absorbed by the fibrous swab 16 of the device being utilized. This basic procedure was utilized in all examples.

In this experiment, the specimen transportation device was a commercially available product, the BBL Port-A-Cul Aerobic Transport Device*. For test purposes, the supplied pledget was removed and a sterile 0.1 gm piece of graphite fiber cloth** was substituted in its place. The inoculated swabs were returned to the outer tube 17 and activated according to the manufacturer's directions in order to bring the media into contact with the pledget and swab. Replicate samples of the devices, both with the standard rayon fiber pledget and the graphite pledget, were stored aerobically at ambient temperatures. At timed intervals of 0, 4, 16, 24, 48, or 72 hours, depending on the organism under study, the swab was used to inoculate a petri plate of an appropriate nutritive agar media. Each inoculated media plate was systematically streaked with a bacteriological loop according to the semi-quantitative "four quadrant method" commonly practiced by those skilled in the art of microbiology.

*BBL Microbiology Systems, Cockeysville, Md. Catalog #21627 for single swab and #21628 for double swab devices. These devices, according to the manufacturer, have a media without agar following the formulation of Amies. The devices are sterilized by radiation and the pledget is a rayon fabric.
**Graphite cloth was obtained from Prodesco, Inc. 700 Park Ave., Perkasie, Pa. The material utilized was a five harness satin weave 1000 filament Thornel TM 300 cloth. Thornel is a trademark of Union Carbide.

Specifically, the plate was inoculated by:
A. Rolling the swab thoroughly over the first quadrant of the plate.
B. Using a standard bacteriological loop, streak back into quadrant 1 eight times.
C. Flame loop and streak back into quadrant 2 four time.
D. Streak back into quadrant 3 twice.

The inoculated plated media were incubated at 37° C.,. Certain organisms were incubated in an atmosphere enriched with 5% carbon dioxide. After twenty four to forty eight hours, the plates were observed for growth and graded according to the following scheme:
4=Growth in quadrant 4 (@ 20 to 100 colonies)
3=Growth in quadrant 3 (@ 20 to 100 colonies)
2=Growth in quadrant 2 (@ 20 to 100 colonies)
1=Growth in quadrant 1 (@ 20 to 100 colonies)
0=No growth
+=Heavy growth (100 colonies)
−=Light growth (20 colonies)

The results of this experiment and a duplicate experiment are summarized in Table 1 (average score for duplicate runs). For each organism tested, the use of the graphite pledget significantly improved the recovery of the organisms. Additionally, for some organisms, the use of the graphite pledget allowed organisms to be recovered at time periods where the control devices showed no growth.

TABLE 1
RECOVERY OF ORGANISMS FROM BBL PORT-A-CUL AEROBIC TRANSPORT DEVICE (w/o agar)

| ORGANISM TESTED | PLEDGET Graphite or Rayon | RECOVERY AFTER INOCULATION ELAPSED INCUBATION TIME (HR) | | | | | |
|---|---|---|---|---|---|---|---|
| | | 0 | 4 | 16 | 24 | 48 | 72 |
| Haemophilus | Graphite | nd | nd | 2+ | 2 | 1− | nd |
| influenzae | Rayon | 3− | 3− | 2− | 1− | 0 | nd |
| Neisseria | Graphite | nd | nd | 2+ | 2− | 1 | nd |
| meningitidis | Rayon | 4− | 2+ | 1+ | 0 | 0 | nd |
| Neisseria | Graphite | nd | nd | 1+ | 1+ | 0 | nd |
| gonorrhoeae | Rayon | 3 | 1 | 0 | 0 | 0 | nd |
| Streptococcus | Graphite | nd | nd | nd | nd | 3+ | 3− |
| pyogenes | Rayon | 4− | nd | nd | nd | 3− | 3 | nd = no determination made

EXAMPLE 2

This experiment was essentially the same as Example 1 with the substitution of specimen transport devices filled with Amies media containing 0.4% agar. The use of the graphite fiber pledget again demonstrated superior recovery of test organisms, as detailed in Table 2.

TABLE 2
RECOVERY OF ORGANISMS FROM AEROBIC TRANSPORT DEVICE w AGAR CONTAINING MEDIA

| ORGANISM TESTED | PLEDGET Graphite or Rayon | RECOVERY AFTER INOCULATION ELAPSED INCUBATION TIME (HR) | | | | | |
|---|---|---|---|---|---|---|---|
| | | 0 | 4 | 16 | 24 | 48 | 72 |
| Haemophilus | Graphite | nd | nd | 2− | 1 | 0 | nd |
| influenzae | Rayon | 2+ | 0 | 0 | 0 | 0 | nd |
| Neisseria | Graphite | nd | nd | 3+ | 3 | 1+ | nd |
| meningitidis | Rayon | 4 | 1+ | 0 | 0 | 0 | nd |
| Neisseria | Graphite | nd | nd | 2+ | 2+ | 0 | nd |
| gonorrhoeae | Rayon | 3 | 2 | 0 | nd | nd | nd |
| Streptococcus | Graphite | nd | nd | nd | nd | 3+ | 3 |
| pyogenes | Rayon | 3+ | nd | nd | nd | 2+ | 2 | nd = no determination made

EXAMPLE 3

In this example, a second commercially available sample transport device was used. The Marion Laboratories Culturette TM device was utilized. As received, this device has a Dacron pledget and was filled with a modified Stuart's media. The media is isolated from the pledget and the swab via containment in a discrete glass ampoule which is crushed to release the media. The standard pledget was replaced with the graphite fiber test material. The smaller size of this device required the use of only 0.05 grams of the graphite cloth. Examination of Table 3 shows the same pattern of enhanced recovery after substitution of the graphite fiber pledget of the invention for the original pledget.

TABLE 3
RECOVERY OF ORGANISMS FROM MARION CULTURETTE AEROBIC TRANSPORT DEVICE

| ORGANISM TESTED | PLEDGET Graphite or Dacron | RECOVERY AFTER INOCULATION ELAPSED INCUBATION TIME (HR) | | | | | |
|---|---|---|---|---|---|---|---|
| | | 0 | 4 | 16 | 24 | 48 | 72 |
| Haemophilus | Graphite | nd | nd | 2 | 2 | 1+ | nd |
| influenzae | Dacron | 3+ | 3− | 2− | 1+ | 0 | nd |
| Neisseria | Graphite | nd | nd | 2 | 2 | 1− | nd |
| meningitidis | Dacron | 4 | 1 | 1− | 0 | 0 | nd |
| Neisseria | Graphite | nd | nd | 2 | 1− | 0 | nd |

TABLE 3-continued
RECOVERY OF ORGANISMS FROM MARION CULTURETTE AEROBIC TRANSPORT DEVICE

| ORGANISM TESTED | PLEDGET Graphite or Dacron | RECOVERY AFTER INOCULATION ELAPSED INCUBATION TIME (HR) | | | | |
|---|---|---|---|---|---|---|
| | | 0 | 4 | 16 | 24 | 48 | 72 |
| gonorrhoeae | Dacron | 3 | 1+ | 0 | nd | nd | nd |
| Streptococcus | Graphite | nd | nd | nd | nd | 2 | 2 |
| pyogenes | Dacron | 3+ | nd | nd | nd | 1+ | 1− | nd = not determined

EXAMPLE 4

This experiment was essentially the same as Example 1 with the substitution of different graphite and carbon cloth materials. These other sources of material again demonstrated superior recovery of test organisms as detailed in Table 4. The substituted materials were as follows:

Graphite-1 was the same cloth described in Example 1.

Graphite-2 was a carbon based cloth woven with Hysol Graphil XA-S 1K fibers produced by Techniweave. This material was sterilized by flaming.

Charcoal cloth was obtained from Johnson & Johnson, New Brunswick, N.J. Material was a component of this firm's Actisorb ™ product and was received sterile.

TABLE 4
RECOVERY OF ORGANISMS FROM BBL PORT-A-CUL AEROBIC TRANSPORT DEVICE (w/o agar)

| ORGANISM TESTED | PLEDGET Graphite Or Rayon | RECOVERY AFTER INOCULATION ELAPSED INCUBATION TIME (HR) | | | | |
|---|---|---|---|---|---|---|
| | | 0 | 2 | 18 | 24 | 48 |
| Haemophilus influenzae | Graphite-1 | 3 | 3 | 2+ | 2+ | 2 |
| | Graphite-2 | 3 | 3 | 2+ | 2+ | 2 |
| | Rayon | 3 | 3− | 1+ | 1 | 0 |
| Neisseria meningitidis | Charcoal cloth | 3+ | nd | 2+ | 2 | 1+ |
| | Rayon | 3− | nd | 1− | 0 | 0 |

What is claimed is:

1. In a microorganism collecting and transporting unit including a tube having an open outer end and a closed inner end, a cap adapted to close said tube, a swabbing device located within said tube including a stem and a swabbing tip on the inner end of said stem, a culture sustaining media located within said tube and a pledget disposed within said tube, said pledget being adapted to keep said swabbing tip moist with said media after a specimen has been collected on said swabbing tip, the improvement comprising utilizing fiber made of carbon or graphite to form at least a portion of one of the members of said transporting unit selected from the group of said pledget and said swabbing tip.

2. A unit in accordance with claim 1 wherein said carbon fiber is a graphite fiber.

3. A unit in accordance with claim 1 wherein said carbon fiber is a carbon fiber.

4. A unit in accordance with claim 1 wherein said graphite fiber is in the form of a woven cloth.

5. A unit in accordance with claim 3 wherein said carbon fiber is in the form of a woven cloth.

* * * * *